US00PP15566P2

(12) United States Plant Patent
Kievit

(10) Patent No.: US PP15,566 P2
(45) Date of Patent: Feb. 15, 2005

(54) ***CALIBRACHOA* PLANT NAMED 'KIECALEM'**

(50) Latin Name: *Calibrachoa procumbens*
Varietal Denomination: Kiecalem

(75) Inventor: Christa Kievit, Venhuizen (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 10/820,514

(22) Filed: Apr. 7, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP14,464 P2 * 1/2004 Pierce ..... Plt./263
PP14,544 P2 * 2/2004 Pierce ..... Plt./263
PP14,779 P2 * 5/2004 Bessho ..... Plt./263

OTHER PUBLICATIONS

UPOV ROM GTITM Computer Database, GTI Jouve Retrieval Software 2004/02 Citation for 'Kiecalem'.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Calibrachoa* plant named 'Kiecalem', characterized by its uniform, low spreading, mounded and trailing plant habit; freely and continuous branching habit; dense and bushy plant growth habit; freely and continuous flowering habit; numerous pale yellow-colored flowers with golden yellow-colored centers; and good garden performance.

1 Drawing Sheet

Botanical classification/cultivar designation: *Calibrachoa procumbens* cultivar Kiecalem.

BACKGROUND OF THE INVENTION

The present Invention relates to a new and distinct cultivar of *Calibrachoa* plant, botanically known as *Calibrachoa procumbens,* and hereinafter referred to by the cultivar name Kiecalem.

The new *Calibrachoa* is a product of a planned breeding program conducted by the Inventor in Venhuizen, The Netherlands. The objective of the breeding program is to create new trailing *Calibrachoas* with numerous flowers with attractive non-fading flower colors and tolerance to high temperatures.

The new *Calibrachoa* originated from a cross-pollination made by the Inventor during in 2000 of two unnamed proprietary *Calibrachoa* seedling selections. The new *Calibrachoa* was selected as a single flowering plant from the resulting progeny of the stated cross-pollination by the Inventor in a controlled environment in 2000 in Venhuizen, The Netherlands.

Asexual reproduction of the new cultivar by terminal cuttings taken in Venhuizen, The Netherlands since 2001 has shown that the unique features of this new *Calibrachoa* are stable and reproduced true to type in successive generations.

SUMMARY OF THE INVENTION

Plants of the cultivar Kiecalem have not been observed under all possible environmental conditions. The phenotype may vary somewhat with variations in environment such as temperature and light intensity without, however, any variance in genotype.

The following traits have been repeatedly observed and are determined to be the unique characteristics of 'Kiecalem'. These characteristics in combination distinguish 'Kiecalem' as a new and distinct cultivar:

1. Uniform, low spreading, mounded and trailing plant habit.
2. Freely and continuous branching habit; dense and bushy plant growth habit.
3. Freely and continuous flowering habit, numerous pale yellow-colored flowers with golden yellow-colored centers.
4. Good garden performance.

Plants of the new *Calibrachoa* differ from the female parent selection primarily in flower color as plants of the female parent selection have white-colored flowers. Plants of the new *Calibrachoa* differ from the male parent selection in plant habit as plants of the new *Calibrachoa* are more trailing than plants of the male parent selection.

Plants of the new *Calibrachoa* can be compared to plants of the *Calibrachoa* cultivar Carillon Lemon, not patented. In side-by-side comparisons conducted in Venhuizen, The Netherlands, plants of the new *Calibrachoa* differed from plants of the cultivar Carillon Lemon in the following characteristics:

1. Plants of the new *Calibrachoa* flowered for a longer period of time than plants of the cultivar Carillon Lemon.
2. Plants of the new *Calibrachoa* flowered more continuously than plants of the cultivar Carillon Lemon.
3. Flowers of plants of the new *Calibrachoa* resisted fading whereas flowers of plants of the cultivar Carillon Lemon faded with development.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the bottom of the sheet comprises a side perspective view of a typical flowering plant of 'Kiecalem' grown in a container.

The photograph at the top of the sheet comprises a close-up view of typical flowers and leaves of 'Kiecalem'.

DETAILED BOTANICAL DESCRIPTION

The aforementioned photographs and following observations and measurements describe plants grown in Lompoc, Calif., under commercial practice during the winter in a polycarbonate-covered greenhouse with day temperatures ranging from 21 to 24° C., night temperatures ranging from 15 to 18° C., and light levels ranging from 4,000 to 8,000 foot candles. When the photographs and the description were taken, plants had been growing for about ten weeks with three plants per 20-cm container. In the following description, color references are made to The Royal Horticultural Society Colour Chart, 1995 Edition, except where general terms of ordinary dictionary significance are used.

Botanical classification: *Calibrachoa procumbens* cultivar Kiecalem.

Parentage:

*Female parent.*—Unnamed proprietary *Calibrachoa procumbens* seedling selection, not patented.

*Male parent.*—Unnamed proprietary *Calibrachoa procumbens* seedling selection, not patented.

Propagation:

*Type cutting.*—Terminal vegetative cuttings.

*Time to initiate roots, summer and winter.*—About two weeks at 21° C.

*Time to develop roots.*—About three weeks at 21° C.

*Root description.*—Fine, fibrous; white in color.

Plant description:

*Form.*—Annual flowering plant; uniform, mounded, low spreading and trailing plant habit; plants eventually becoming hemispherical to spherical in shape. Freely and continuously branching habit with about five main lateral branches per plant with lateral branches forming potentially at every node; dense and bushy plant growth habit. Vigorous growth habit.

*Usage.*—Appropriate for hanging baskets, window boxes, patio containers and landscape applications.

*Plant height.*—About 9 cm.

*Plant diameter, single plant.*—About 24 cm.

*Lateral branches.*—Length: About 18 cm. Diameter: About 2 mm. Internode length: About 1.5 cm. Texture: Pubescent; viscid. Color: 145A.

*Foliage description.*—Arrangement: Before flowering, alternate; after flowering, opposite; simple. Length: About 4 cm. Width: About 1.4 cm. Shape: Elliptic. Apex: Broadly acute. Base: Attenuate. Margin: Entire. Texture, upper and lower surfaces: Sparsely pubescent; coarse; viscid. Venation pattern: Pinnate, arcuate. Color: Developing foliage, upper surface: 146B. Developing foliage, lower surface: 144B. Fully expanded foliage, upper surface: 146A. Fully expanded foliage, lower surface: 146B. Venation, upper surface: 146C. Venation, lower surface: 147C. Petiole length: About 6 mm. Petiole diameter: About 1.5 mm. Petiole color: 144A.

Flower description:

*Flower type and habit.*—Salverform flowers; single, axillary. Flowers face mostly upward or outward and are held above and beyond the foliage.

*Quantity of flowers.*—Freely flowering, typically about thirteen to fourteen open flowers and flower buds per lateral stem.

*Natural flowering season.*—Long day responsive; spring until frost in the autumn; flowering continuous during the flowering period. Flowers persistent.

*Flower longevity on the plant.*—About 10 to 14 days.

*Fragrance.*—None detected.

*Flower diameter.*—About 3 cm.

*Flower depth (height).*—About 3.1 cm.

*Flower throat diameter.*—About 8 mm.

*Flower buds (showing color).*—Length: About 2 cm. Diameter: About 4 mm. Shape: Elongated oblong. Color: 3C.

*Corolla.*—Arrangement/appearance: Single whorl of five petals, fused into flared trumpet with distinct clefts between petal lobes. Petal length from throat: About 1.1 cm. Petal width: About 1.3 cm. Petal shape: Roughly spatulate or fan-shaped. Petal apex: Rounded. Petal margin: Entire. Petal texture, upper and lower surfaces: Smooth, velvety. Color: Petal, upper surface, when opening: 4D. Petal, lower surface, when opening: 155A. Petal, upper surface, fully opened: 8C to 8D; towards the margins, 155A. Petal, lower surface, fully opened: 10D. Flower throat (inside): 12A. Flower tube (outside): 11B. Venation, upper and lower petal surfaces: Close to 12A.

*Sepals.*—Arrangement/appearance: Single whorl of five sepals fused at base, star-shaped. Length: About 1 cm. Width: About 2.5 mm. Shape: Lanceolate. Apex: Acute. Margin: Entire. Texture, upper and lower surfaces: Pubescent. Color, immature and mature, upper and lower surfaces: 144B.

*Peduncles.*—Length: About 1.5 cm. Width: About 1 mm. Angle: About 45° to the stem. Strength: Strong. Texture: Pubescent. Color: 144B.

*Reproductive organs.*—Stamens: Quantity/arrangement: Five. Anther shape: Rounded. Anther length: Less than 1 mm. Anther color: 3B. Pollen amount: Scarce. Pollen color: 3B. Pistils: Quantity: One. Pistil length: About 9 mm. Stigma shape: Rounded. Stigma color: 145A. Style length: About 7 mm. Style color: 145D. Ovary color: 145B.

*Seed/fruit.*—Seed and fruit production has not been observed.

Disease/pest resistance: Plants of the new *Calibrachoa* have not been noted to be resistant to pathogens or pests common to *Calibrachoa.*

Garden performance: Plants of the new *Calibrachoa* have good garden performance and have been observed to be tolerant to rain, wind and temperatures ranging from 8 to 35° C.

It is claimed:

1. A new and distinct cultivar of *Calibrachoa* plant named 'Kiecalem', as illustrated and described.

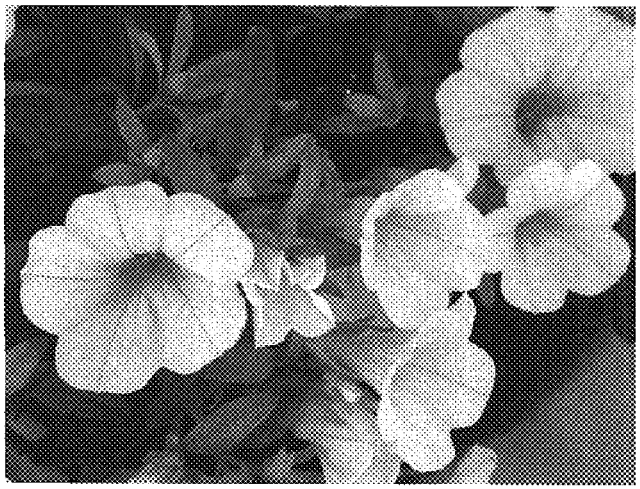
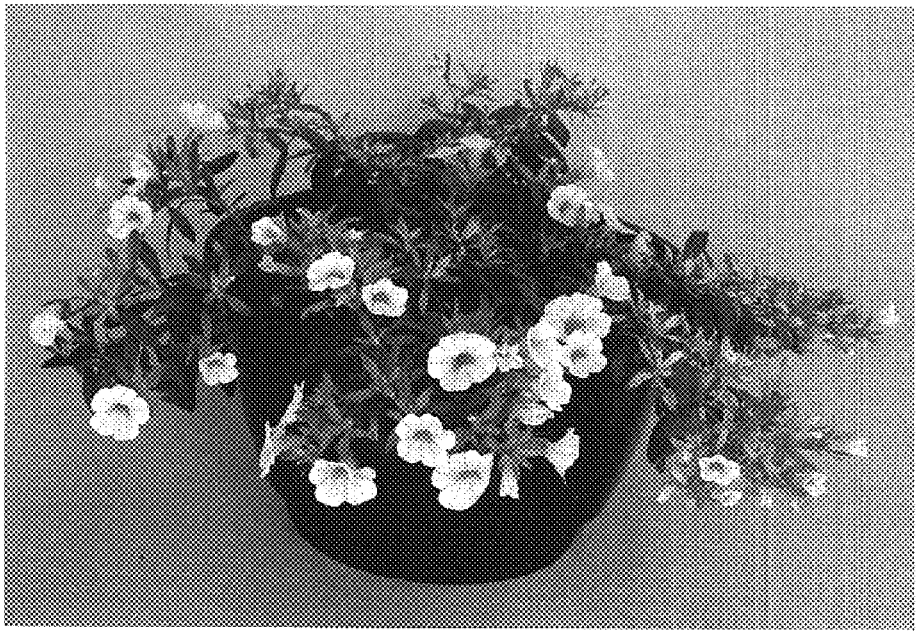

* * * * *